(12) United States Patent
Bihler et al.

(10) Patent No.: US 12,343,539 B2
(45) Date of Patent: Jul. 1, 2025

(54) IMPLANT COMPRISING EMBEDDED CONDUCTOR TRACK AND PRODUCTION METHOD

(71) Applicant: DYCONEX AG, Bassersdorf (CH)

(72) Inventors: Eckardt Bihler, Uitikon (CH); Marc Hauer, Uster (CH); Dirk Muessig, West Linn, OR (US)

(73) Assignee: Dyconex AG, Bassersdorf (CH)

( * ) Notice: Subject to any disclaimer, the term of this patent is extended or adjusted under 35 U.S.C. 154(b) by 0 days.

(21) Appl. No.: 17/892,184

(22) Filed: Aug. 22, 2022

(65) Prior Publication Data

US 2022/0395688 A1 Dec. 15, 2022

Related U.S. Application Data

(63) Continuation of application No. 16/972,072, filed as application No. PCT/EP2019/067373 on Jun. 28, 2019, now Pat. No. 11,446,503.

(30) Foreign Application Priority Data

Jul. 6, 2018 (DE) ...................... 10 2018 211 186.3

(51) Int. Cl.
*A61N 1/36* (2006.01)
*A61N 1/372* (2006.01)
*A61N 1/375* (2006.01)

(52) U.S. Cl.
CPC ...... *A61N 1/36125* (2013.01); *A61N 1/37211* (2013.01); *A61N 1/375* (2013.01); *A61N 1/37512* (2017.08); *A61N 1/3754* (2013.01)

(58) Field of Classification Search
CPC ...................... A61N 1/36125; A61N 1/37211; A61N 1/375; A61N 1/37512; A61N 1/3754; A61B 5/24; A61B 5/291; A61B 2562/0247

See application file for complete search history.

(56) References Cited

U.S. PATENT DOCUMENTS

| 6,358,281 | B1 | 3/2002 | Berrang et al. |
| 11,446,503 | B2 * | 9/2022 | Bihler ................ A61N 1/36125 |

(Continued)

FOREIGN PATENT DOCUMENTS

| DE | 69629305 T2 | 5/2004 |
| EP | 0844899 B1 | 7/2003 |

(Continued)

OTHER PUBLICATIONS

German Search Report for German Case No. DE 10 2018 211 186.3, dated Mar. 1, 2019 (7 pages).

(Continued)

*Primary Examiner* — Catherine M Voorhees
(74) *Attorney, Agent, or Firm* — Buchanan Ingersoll & Rooney PC

(57) ABSTRACT

The disclosure relates to an implant comprising a substrate, a housing, wherein the housing is disposed on the substrate, an electronic circuit disposed on the substrate inside the housing, an electronic component disposed on the substrate outside the housing, and a conductor track, wherein the conductor track connects the electronic circuit to the electronic component. The conductor track is embedded into the substrate at least in sections in such a way that at least one section of the conductor track is completely surrounded by the substrate. Furthermore, a method for creating an implant is disclosed.

14 Claims, 3 Drawing Sheets

(56) References Cited

U.S. PATENT DOCUMENTS

| | | | |
|---|---|---|---|
| 2013/0333918 A1 | 12/2013 | Lotfi | |
| 2014/0163646 A1* | 6/2014 | Tischendorf | A61N 1/0551 |
| | | | 607/116 |
| 2015/0283374 A1 | 10/2015 | Kronmueller et al. | |
| 2017/0359924 A1 | 12/2017 | Hauer | |
| 2020/0206544 A1* | 7/2020 | Vaughan | A62B 17/04 |
| 2021/0052783 A1* | 2/2021 | Adams | A61F 9/0017 |
| 2021/0106815 A1* | 4/2021 | Smith | A61N 1/3758 |
| 2021/0121704 A1 | 4/2021 | Bihler et al. | |

FOREIGN PATENT DOCUMENTS

| | | | |
|---|---|---|---|
| EP | 2714191 | B1 | 2/2017 |
| EP | 2440025 | B1 | 5/2017 |

OTHER PUBLICATIONS

International Search Report (PCT/ISA/210) and Written Opinion (PCT/ISA/237) mailed on Nov. 11, 2019, by the European Patent Office as the International Searching Authority for International Application No. PCT/EP2019/067373.

* cited by examiner

IMPLANT COMPRISING EMBEDDED CONDUCTOR TRACK AND PRODUCTION METHOD

CROSS-REFERENCE TO RELATED APPLICATIONS

This application is a continuation application of co-pending U.S. application Ser. No. 16/972,072, filed on Dec. 4, 2020, which is a U.S. National Phase under 35 U.S.C. § 371 of PCT International Patent Application No. PCT/EP2019/067373, filed on Jun. 28, 2019, which claims the benefit of German Patent Application No. 10 2018 211 186.3, filed on Jul. 6, 2018, the disclosures of which are hereby incorporated by reference herein in their entireties.

TECHNICAL FIELD

The present disclosure relates to an implant comprising an embedded conductor track and to a production method for an implant.

BACKGROUND

Implants, such as cardiac pacemakers, usually comprise a housing made of titanium, which surrounds the electronic components of the implant (printed circuit board, battery). At least one feedthrough is formed in the housing to establish electrical contact outside the housing, for example for an electrode connection. Forming the feedthrough in the titanium housing is a complex task.

European Publication No. EP 2 714 191 B1 discloses an implant comprising a printed circuit board made of liquid crystal polymer and a housing made of liquid crystal polymer. The printed circuit board is fused to edge regions of the housing so as to achieve a hermetic seal.

European Publication No. EP 2 440 025 B1 discloses the use of a heating wire for fusing a substrate to a housing disposed on the substrate.

The present disclosure is directed toward overcoming one or more of the above-mentioned problems, though not necessarily limited to embodiments that do.

SUMMARY

It is an object of the present invention to provide improved technologies for an implant. In particular, an electrical contact is to be established in a simple manner with a region outside an implant housing. Furthermore, components of the implant are to be protected against contact with body fluid.

An implant and a method for creating an implant according to the independent claims are disclosed. Further embodiments are the subject matter of dependent claims.

According to one aspect, an implant is provided. The implant comprises a substrate and a housing, the housing being disposed on the substrate. An electronic circuit is disposed on the substrate inside the housing. An electronic component is disposed on the substrate outside the housing. The implant moreover comprises a conductor track, wherein the conductor track connects the electronic circuit to the electronic component. The conductor track is embedded into the substrate at least in sections in such a way that at least one section of the conductor track is completely surrounded by the substrate. It is not necessary to form a feedthrough in the housing or in the substrate. The related necessary complex steps are avoided. Furthermore, the embedded section of the conductor track is protected against contact with body fluid.

Another aspect relates to a method for creating an implant. The method includes the following steps: providing a substrate, disposing an electronic circuit on the substrate, disposing a housing on the substrate in such a way that the electronic circuit is disposed inside the housing, disposing an electronic component on the substrate outside the housing, and establishing a connection between the electronic circuit and the electronic component by way of a conductor track, wherein the conductor track is embedded into the substrate at least in sections in such a way that at least one section of the conductor track is completely surrounded by the substrate.

The housing surrounds an interior space. The electronic circuit is disposed in the interior space of the housing. The electronic component is disposed outside the housing (that is, outside the interior space). The electronic circuit and the electronic component are spatially separated.

The housing can be disposed on the substrate in such a way that the interior space is hermetically sealed. The interior space of the housing can be filled with a gas or a plastic material. Suitable gases are noble gases (such as helium) or other inert gases (such as nitrogen or carbon dioxide). The plastic material can be liquid crystal polymer (LCP), for example, or a potting compound made of epoxy resins or silicones. The filling can be used to stabilize the components or to generate a space that exhibits low (chemical) reactivity.

The housing can be coated with a diffusion barrier, for example with a metal layer, in sections or in its entirety. Suitable metals are palladium, gold, platinum and titanium.

One or more heating elements can be formed in the substrate. The housing can be disposed on the substrate in such a way that edges of the housing rest on the heating elements. Heating the heating elements allows the edges of the housing and the material of the substrate surrounding the heating elements to be made to melt, so that the materials of the housing and of the substrate bond with one another and, after cooling, form an integral bond. The heating element or heating elements can be implemented in the form of titanium wire or gold wire.

The implant can be an active implant, for example for neurostimulation, biomonitoring, biosensing, brain interface or neurosensing. The implant can comprise an energy store (for example, a battery). The energy store can be disposed in the housing. The energy store can be configured to supply the electronic circuit with energy.

The conductor track can be completely embedded into the substrate in such a way that the conductor track is surrounded by the substrate over the entire length thereof.

The electronic component can be an electrode or a sensor. The electrode can be designed as a planar electrode. The sensor can be a pressure sensor (for example, a microelectromechanical (MEMS) pressure sensor, a photodiode or a laser diode.

The electronic circuit can comprise multiple electronic components, such as a processor and a memory. The electronic circuit can be configured to record and process signals detected by the electronic component.

It is possible for multiple electronic components to be disposed on the substrate outside the housing, wherein the multiple electronic components are connected to the electronic circuit by way of multiple conductor tracks, and wherein the multiple conductor tracks are embedded into the substrate at least in sections in such a way that, for each conductor track, at least one section of the respective conductor track is completely surrounded by the substrate. The multiple conductor tracks can be completely embedded into the substrate. The multiple electronic components can be multiple electrodes and/or multiple sensors, for example.

It may be provided that the substrate is a multi-layer substrate and that at least one section of the conductor track is embedded between two layers of the multi-layer substrate. The conductor track can be disposed completely (across the entire length thereof) between two layers of the multi-layer substrate. The multiple layers of the substrate can be made of the same material, for example of a thermoplastic (such as LCP). The multiple layers can also be made of different materials, for example one of the layers may also be made of a metal. For example, biocompatible stainless steels or Nitinol may be used for this purpose.

The substrate can be made of a thermoplastic, such as LCP. The substrate can be made of a flexible material.

The housing can be made of a thermoplastic, such as LCP.

The substrate and the housing can be made of the same material, for example a thermoplastic such as LCP.

A second housing can be disposed on the substrate, wherein a second electronic circuit is disposed on the substrate inside the second housing. The comments made with respect to the housing apply analogously to the second housing.

The housing comprising the electronic circuit and the second housing comprising the second electronic circuit can be disposed on the same side of the substrate.

The housing and the second housing can be disposed at a distance from one another, wherein the substrate is flexible in a region between the housing and the second housing.

The housing comprising the electronic circuit can be disposed on a first side of the substrate, and the second housing comprising the second electronic circuit can be disposed on a second side of the substrate, the second side being situated opposite the first side.

A coil can be integrated in the housing. The coil can be configured to communicate with another device, for example a programming device.

The electronic circuit can be mounted onto a flexible printed circuit board made of LCP using a conventional and known mounting technique. If necessary, a battery and/or electrode wires can be connected to the flexible printed circuit board by way of laser or resistance welding. The entire assembly can be covered with a prefabricated protective cap made of injection-molded LCP. The protective cap can be welded to the flexible printed circuit board in a hermetically sealed manner by local fusion of LCP material, for example. Moreover, a metal layer can be applied onto the entire structure as a diffusion barrier.

Features disclosed in connection with the implant can be applied analogously to the method, and vice versa.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

Exemplary embodiments will be described hereafter in greater detail with reference to the figures. In the drawings.

DETAILED DESCRIPTION

Figure 1:
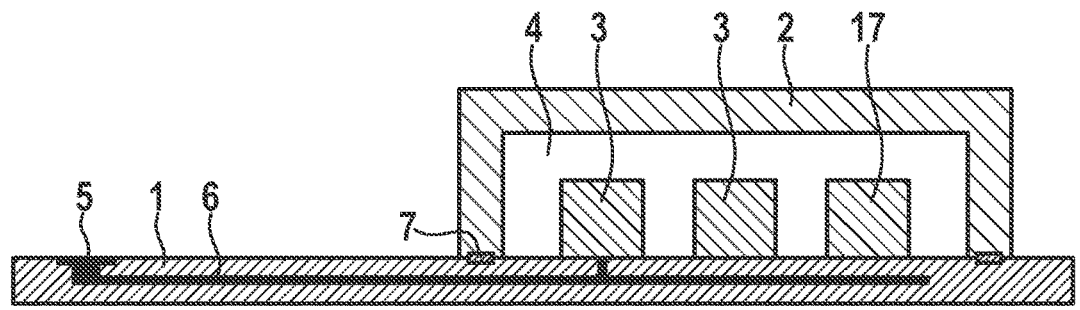
FIG. 1 shows a side view of a first embodiment of the implant.

Hereafter, the same reference numerals are used for identical components.

FIG. 1 shows a first embodiment of the implant. The implant comprises a substrate 1 and a first housing 2. The first housing 2 is disposed on the substrate 1 so that an interior space 4 is hermetically sealed with respect to the surrounding area. A first electronic circuit 3 and a battery 17 are disposed inside the first housing 2 (that is, in the interior space 4). The battery 17 is connected to the first electronic circuit 3, supplying it with electric energy. An electronic component 5 is disposed on the substrate outside the first housing 2. The electronic component 5 is connected to the first electronic circuit 3 by way of a conductor track 6. The conductor track 6 is embedded into the substrate 1, so that the conductor track 6 is surrounded by the substrate 1 across the entire length thereof. A first heating element 7 is disposed on the substrate 1. Edges of the first housing 2 are disposed on the heating element. Heating of the first heating element 7 prompts the materials of the substrate 1 and of the first housing 2 to melt in the area around the heating element. After cooling, the first housing 2 is fixedly joined to the substrate 1 (thermal welded joint).

The substrate 1 can be a multi-layer substrate and comprise two layers, for example. The layers of the substrate 1 can be made of LCP. The first housing 2 can likewise be made of LCP. The first electronic circuit 3 can be implemented in the form of a printed circuit assembly. Components of the first electronic circuit 3 can be designed as surface-mounted devices (SMD). The interior space 4 of the first housing 2 can be filled with a gas or a plastic material. The conductor track 6 can be made of a biocompatible material, such as gold or titanium. In the event of mechanical damage to the implant, biocompatible metals are advantageous. As an alternative, the conductor track 6 can be made of copper.

So as to hermetically decouple the first electronic circuit 3 together with the battery 17 from the body fluid, the first housing 2 is placed on the substrate 1. The first housing 2 is joined to the substrate 1 by local fusion of the materials of the two components (such as LCP). In one embodiment, a flexible printed circuit board, to which a heating element is applied at the joining sites, is introduced between the first housing 2 and the substrate 1 (not shown). As an alternative, the first heating element 7 can also be integrated directly into the substrate 1. The heating element is made, for example, of a thin layer of titanium (for example, 100 nm to 500 nm layer thickness) or of a thin gold layer (for example, 100 nm titanium and 500 nm gold) and is connected to an external power source via a connecting structure (for example, made of copper) outside the first housing 2.

In the case of a multi-layer substrate, the conductor track 6 is situated between two flexible printed circuit boards of the substrate 1, which are each coated with LCP melting at a low temperature, so that the surrounding areas comprising LCP having a low melting point melt completely when the heating element is heated to temperatures above the melting temperature of the LCP having a low melting point (approximately 250 to 300° C.) and establish a form-locked joint between the first housing 2, the two flexible printed circuit boards of the substrate 1 and the conductor track 6. A metal layer or a thin sheet made of metal can be applied to the opposite side to mechanically reinforce the substrate 1.

Figure 2:
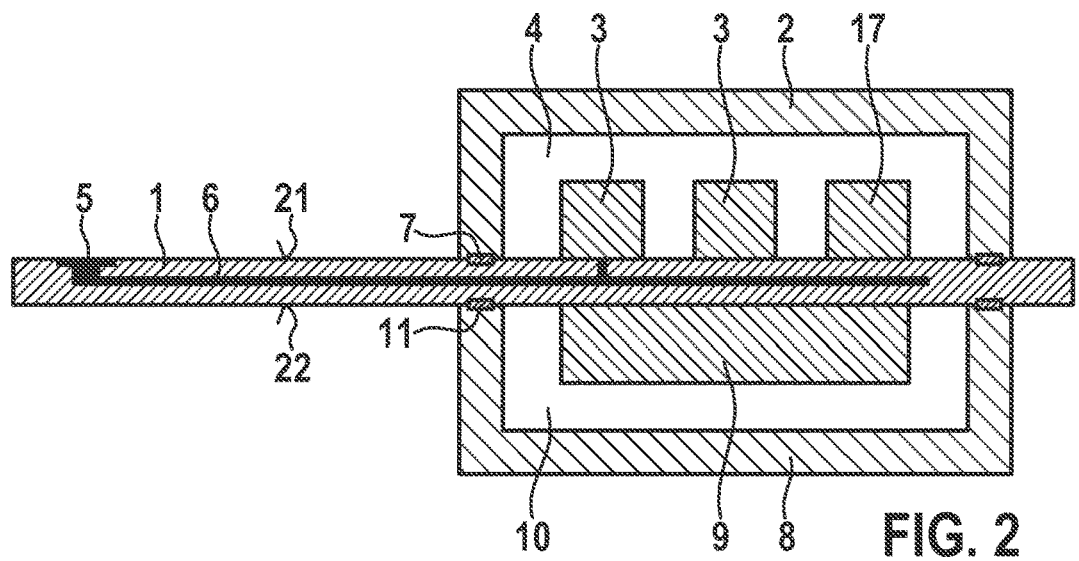
FIG. 2 shows a side view of a second embodiment of the implant.

In one embodiment, a second housing 8 is attached in the same manner on the opposite side of the substrate 1 (FIG. 2). The two housings can be attached together in one operation. The conductor track 6 should at least extend over a distance of 0.1 mm to 0.3 mm inside fused LCP to establish a sufficient diffusion barrier.

Afterwards, the assembly can be metallized together with the first housing 2 to create a further diffusion barrier. The coating comprising a biocompatible metal (such as palladium, gold, platinum or titanium) can be carried out either chemically or by way of a vacuum process. An additional diffusion barrier is applied by the applied metal layer, which blocks possible diffusion pathways along the boundary layers between the various layers of the substrate 1. A hermetic housing is thus created, which offers long-term stability and is able to remain in the body of a patient for at least the service life of the battery.

FIG. 2 shows a second embodiment of the implant. In addition to the embodiment shown in FIG. 1 (where all components are disposed on a first side 21, which is here the top side of the substrate 1), further components, these being a second housing 8 and a second electronic circuit 9, are disposed on a second side 22, which is here the bottom side of the substrate 1. The second electronic circuit 9 is disposed inside the second housing 8 (in an interior space 10 of the second housing 8). The second electronic circuit 9 can be connected to the electronic component 5 by way of a further conductor track embedded into the substrate 1 (not shown). A second heating element 11, to which the second housing 8 is attached on the second side 22 of the substrate 1 by fusion, is disposed on the second side 22 of the substrate 1.

Figure 3:
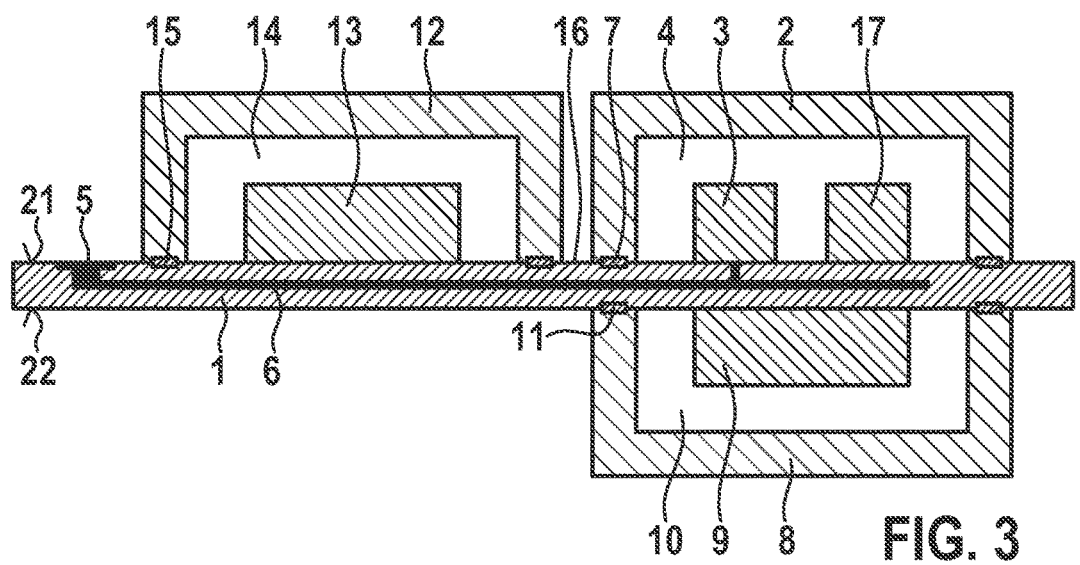
FIG. 3 shows a side view of a third embodiment of the implant.

A third embodiment of the implant is shown in FIG. 3. In addition to the embodiment shown in FIG. 2, a third housing 12 and a third electronic circuit 13 are disposed on the first side 21 of the substrate 1. The third electronic circuit 13 is disposed inside the third housing 12 (in an interior space 14 of the third housing 12). The third electronic circuit 13 can be connected to the electronic component 5 by way of a further conductor track embedded into the substrate 1 (not shown). A third heating element 15, to which the third housing 12 is attached on the first side 21 of the substrate 1 by fusion, is disposed on the substrate 1. A flexible region 16 of the substrate 1 is formed between the first housing 2 and the third housing 12.

Figure 4:
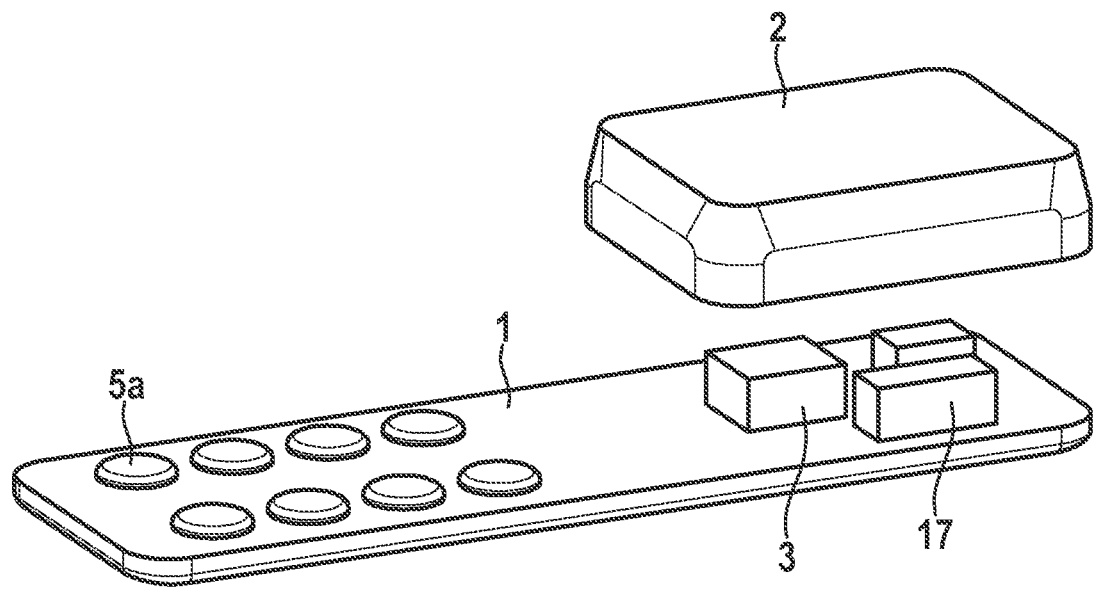
FIG. 4 shows a perspective view of a fourth embodiment of the implant.

The embodiment shown in FIG. 4 essentially corresponds to the embodiment according to FIG. 1. The electronic component is implemented in the form of eight electrodes 5*a* here. A different number of electrodes is likewise possible.

Figure 5:
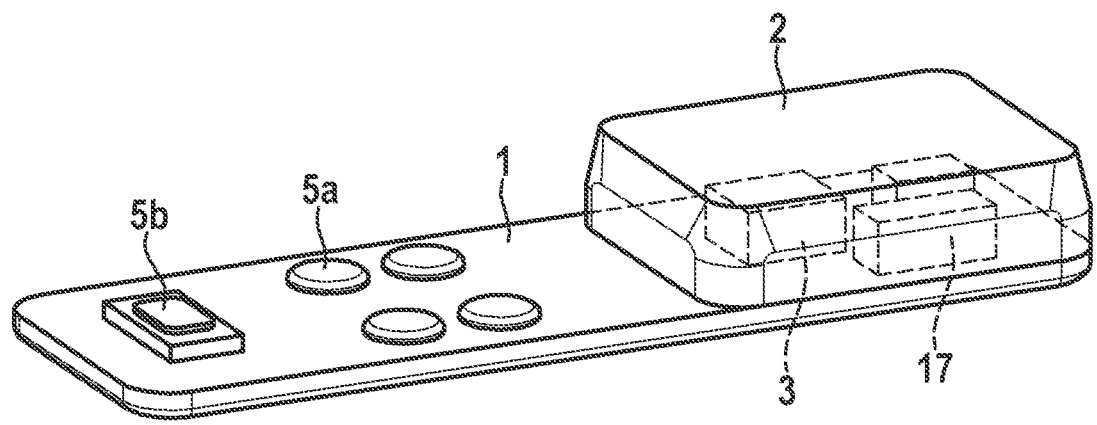
FIG. 5 shows a perspective view of a fifth embodiment of the implant.

In the embodiment shown in FIG. 5, the electronic component is designed as a combination of electrodes 5*a* and a sensor 5*b*.

Figure 6:
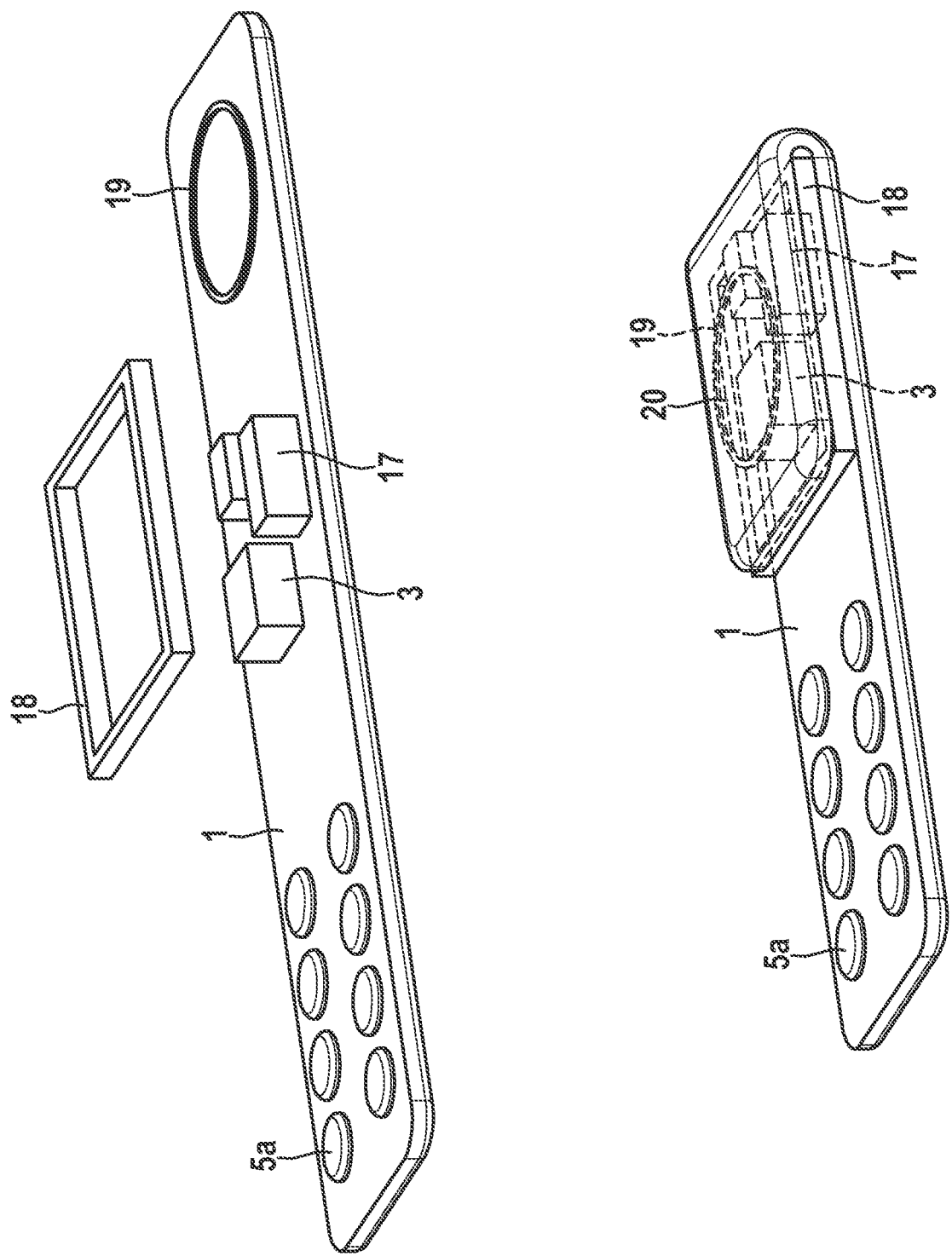
FIG. 6 shows a perspective view of a sixth embodiment of the implant. The top portion of FIG. 6 shows a preliminary stage of the assembly of the implant. The bottom portion of FIG. 6 shows the assembled implant.

A further embodiment is shown in FIG. 6. A frame 18 is disposed on the substrate 1 in such a way that the frame 18 surrounds the first electronic circuit 3 and the battery 17. A section of the substrate 1 is folded over, so that the section rests on the frame 18 and forms a cover 20. The frame 18 and the cover 20 form a closed area in which the first electronic circuit 3 and the battery 17 are disposed. Electrodes 5*a* are disposed on the substrate 1 outside the closed area. A coil 19, which is configured to communicate with an external device, is integrated into the folded-over section (cover 20). The frame 18 can be made of LCP. Electrodes can be disposed both inside and outside the closed area on the second or bottom side of the substrate 1.

The technical teaching disclosed here allows implants, for example implantable pulse generators or monitors, to be produced in a considerably simpler, miniaturized and cost-effective manner.

The features disclosed in the description, the claims and the figures can be relevant for the implementation of embodiments either alone or in any random combination with one another.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

LIST OF REFERENCE NUMERALS

1 substrate
2 first housing
3 first electronic circuit
4 interior space of the first housing
5 electronic component
5*a* electrode
5*b* sensor
6 conductor track
7 first heating element
8 second housing
9 second electronic circuit
10 interior space of the second housing
11 second heating element
12 third housing
13 third electronic circuit
14 interior space of the third housing
15 third heating element
16 flexible region of the substrate
17 battery
18 frame
19 coil
20 cover
21 first side of the substrate
22 second side of the substrate

The invention claimed is:
1. An implant comprising:
a substrate made of thermoplastic;
a housing made of thermoplastic, wherein the housing is disposed on the substrate;
a hermetic seal joining the housing and substrate together, wherein the hermetic seal is formed via heating and melting an interface of the substrate and the housing;
a diffusion barrier comprising a metal layer applied to the housing and substrate;
an electronic circuit disposed on the substrate inside the housing;
an electronic component disposed on the substrate outside the housing;

conductor track, wherein the conductor track connects the electronic circuit to the electronic component;

wherein the conductor track is embedded into the substrate at least in sections so that at least one section of the conductor track is completely surrounded by the substrate.

2. The implant according to claim 1, wherein the conductor track is completely embedded into the substrate so that the conductor track is surrounded by the substrate across the entire length thereof.

3. The implant according to claim 1, wherein the electronic component is an electrode or a sensor.

4. The implant according to claim 1, wherein multiple electronic components are disposed on the substrate outside the housing, the multiple electronic components being connected to the electronic circuit by way of multiple conductor tracks, and the multiple conductor tracks being embedded into the substrate at least in sections so that, for each conductor track, at least one section of the respective conductor track is completely surrounded by the substrate.

5. The implant according to claim 1, wherein the substrate is a multi-layer substrate, and at least one section of the conductor track is embedded between two layers of the multi-layer substrate.

6. The implant according to claim 1, wherein the substrate and the housing are made of the same material.

7. The implant according to claim 1, wherein a second housing is disposed on the substrate, and a second electronic circuit is disposed on the substrate inside the second housing.

8. The implant according to claim 7, wherein the housing comprising the electronic circuit and the second housing comprising the second electronic circuit are disposed on the same side of the substrate.

9. The implant according to claim 8, wherein the housing and the second housing are disposed at a distance from one another, and the substrate is flexible in a region between the housing and the second housing.

10. The implant according to claim 7, wherein the housing comprising the electronic circuit is disposed on a first side of the substrate, and the second housing comprising the second electronic circuit is disposed on a second side of the substrate, the second side being situated opposite the first side.

11. The implant according to claim 1, wherein a coil is integrated into the housing.

12. The implant of claim 1, wherein the metal layer comprises a biocompatible metal.

13. The implant of claim 12, wherein the biocompatible metal comprises at least one of palladium, gold, platinum and titanium.

14. An implant comprising:
a substrate made of a thermoplastic;
a housing made of a thermoplastic, wherein the housing is disposed on the substrate;
a hermetic seal joining the housing and substrate together, wherein the hermetic seal is formed via heating and melting an interface of the substrate and the housing;
a diffusion barrier comprising a metal layer applied to the housing and substrate;
an electronic circuit disposed on the substrate inside the housing;
an electronic component disposed on the substrate outside the housing;
conductor track, wherein the conductor track connects the electronic circuit to the electronic component;
wherein the conductor track is embedded into the substrate at least in sections so that at least one section of the conductor track is completely surrounded by the substrate;
wherein the housing is coated in sections or in its entirety with a metal layer.

* * * * *